United States Patent [19]

Hohenberg et al.

[11] Patent Number: 5,052,425
[45] Date of Patent: Oct. 1, 1991

[54] METHOD AND APPARATUS FOR CONTINUOUS REMOVAL OF A SUB-QUANTITY FROM A GAS STREAM

[75] Inventors: Guenter Hohenberg; Heimo Denk, both of Graz, Austria

[73] Assignee: AVL Gesellschaft fuer Verbrennungskraftmaschinen und Messtechnik mbH. Prof. Dr. Dr. h.c. Hans List, Austria

[21] Appl. No.: 492,827

[22] Filed: Mar. 13, 1990

[30] Foreign Application Priority Data

Mar. 13, 1989 [AT] Austria ............................. A575/89

[51] Int. Cl.⁵ ............................................. F16K 11/00
[52] U.S. Cl. ..................................... 137/1; 73/863.03; 73/863.58; 137/8; 137/118; 137/605; 137/897; 422/83
[58] Field of Search ........... 73/863.03, 863.23, 863.58, 73/864.21; 137/1, 8, 118, 110, 605, 597, 896, 897, 803, 806; 422/83

[56] References Cited

U.S. PATENT DOCUMENTS

| | | | |
|---|---|---|---|
| 3,478,600 | 11/1969 | Lynn | 73/863.03 X |
| 3,665,949 | 5/1972 | Rivard | 137/806 |
| 3,760,831 | 9/1973 | Colvin | 422/83 X |
| 4,091,835 | 5/1978 | Frampton | 73/863.03 X |
| 4,814,143 | 3/1989 | Kojima | 422/83 |

*Primary Examiner*—Robert G. Nilson
*Attorney, Agent, or Firm*—Hill, Van Santen, Steadman & Simpson

[57] ABSTRACT

A method and apparatus for controlling the volume stream of a sub-quantity which is continuously removed from a gas stream and which is supplied and mixed with a gaseous dilutant stream, the sub-quantity is conducted from the main stream through a back-up region where the control of the flow of sub-quantity without affecting its composition is effected by a counterflow in a back-up region which is controllably directed in opposition to the sub-quantity flow such as by an annular upstream directed gap surrounding the sub-quantity conduit or by openings which are directed in a direction against the sub-quantity flow or by a pipe directing a flow against the discharge end of the sub-quantity flow. The sub-quantity flow is mixed in a mixing tunnel with a dilution gas and a small quantity of this mixed gas is removed for testing.

19 Claims, 2 Drawing Sheets

METHOD AND APPARATUS FOR CONTINUOUS REMOVAL OF A SUB-QUANTITY FROM A GAS STREAM

BACKGROUND OF THE INVENTION

This invention relates to improvements in methods and apparatus for the continuous removal of a sub-quantity representative test quantity from a gas stream and for the continuous mixing of the test quantity with a dilutant gas stream. The sub-quantity is removed and branched off from a main gas flow stream such as the exhaust stream from a diesel engine. A counter-pressure is employed to act on the sub-quantity from the dilutant stream to control the volume stream of the sub-quantity. The invention also relates to an improved apparatus for utilizing the method of the invention including a probe line which branches off of the sub-quantity discharge line and a mixing tunnel in which the downstream end of the sub-quantity removal and a delivery line carrying the dilutant stream discharge for mixing the gases.

The method and apparatus of the invention are particularly well suited for measuring processes to determine characteristics of a gas stream where only a representative sub-quantity may be examined to avoid any material disruption of the main gas stream and to accommodate required dimensioning of measuring instruments. Also, applications utilizing the method are possible which serve to produce gas mixtures for a variety of other uses. For example, analysis of constituents in suspended material in gases from chemical processes may be accomplished. One particular use is the measurement of exhaust gases from internal combustion engines and particularly diesel engines. In the case of measuring the exhaust gases, it is frequently necessary to dilute the gas stream to be analyzed with other gaseous dilutant streams such as air. In such employment, dilutant tunnels are used where a test sample is fed for measuring the particle emission of the diesel engines. The exhaust gas of the engine is introduced into the dilutant tunnel and is uniformly mixed with pure air in a turbulent flow in order to simulate the emission conditions. It is frequently desirable for space and performance reasons to extract only a sub-quantity from the gas stream and to examine this after dilution. A critical problem in such gas stream dilution is the control of the sub-quantity removed since it is usually not appropriate to directly control the stream of the sub-quantity with throttle valves or similar mechanisms, and the influence or variation of the composition of the sub-quantity by its removal must be avoided under all circumstances to obtain a proper test mount. In a method of testing and diluting the substream of diesel exhaust gas, for example, the pressure in the diluting system or dilutant stream has been varied by respective blowers arranged at the input side and output side of the diluting system. As a result of this, the counter-pressure acting on the sub-quantity from the dilutant stream at the downstream side is directly influenced, and thus the volume of the sub-quantity is affected or controlled. This method heretofore used and the apparatus used for this has critical disadvantages.

The temperature of the dilutant stream being mixed with the sub-quantity rises as a consequence of the pressure elevation of the dilutant stream at the input side as well as a result of compressor losses that occur. This has an influence on the measurement of the sub-stream. To avoid this, this requires a relatively involved cooling of the dilutant stream. In the particle measurement of diesel exhaust gases, for example, an admission temperature of the dilutant air of $25\pm5°$ C. as well as a maximum temperature of $52°$ C. of the gas sample ultimately examined are prescribed for satisfactory results.

As a result of utilizing the foregoing known principles, an exhaust arrangement acting on the diluting stream at the output side must be controlled with a full throughput quantity of the dilutant stream which requires a rather high powered drive and correspondingly a high outlay for the control is thus required. Another critical disadvantage of the method and arrangement heretofore known results in that there is a maximum counter-pressure that can operate in the exhaust gas flow system of a diesel motor. This is important because a relatively high gas counter-pressure (such as up to about 250 mbar) can appear in certain operating points with the us of various exhaust system configurations, and specifically with soot filters. When it is desired to control the pressure in the actual diluting system via the exhaust mechanism at the output side, then in addition to causing increase in the drive power of the blower, this results in a further temperature elevation of the dilutant air and further aggravates the cooling problems.

FEATURES OF THE INVENTION

It is an object of the present invention to avoid the disadvantages of methods heretofore used such as those recited above and to provide a method and apparatus which makes it possible to control the volume stream of a sub-quantity of branched off gas by a simple means which has no adverse influence on the measurement of the gas or upon the reuse of the diluted sub-quantity. A further object of the invention is to provide an improved apparatus and method for removal of a test or sub-quantity of gas taken from a main flow, such as a diesel engine exhaust, and to accurately mix the test quantity with a dilution gas such that a mixing is accomplished in a manner where the test sub-quantity can be accurately measured and be an accurate representation of the main gas flow.

In accordance with a feature of the invention, the method of the present invention operates to remove a sub-quantity from a main gas flow and to conduct the sub-quantity through a back-up region before being mixed with a dilutant stream. The back-up region is supplied with a controllable control stream that has elevated pressure in comparison to the dilutant stream. The apparatus for practicing the method provides a back-up region and the sub-quantity removal lien in the back-up region, a control line carries a control stream controllable dependent upon the pressure of the gas stream in the main flow line discharging the sub-quantity into this back-up region. A form o pneumatic diaphragm is created and the volume stream of the sub-quantity which actually ensues for continuous mixing with the dilutant stream can be controlled without any mechanical influence being necessary. Any possibility of premature particle settling and thus false variation or interpretation of the measured value is thus avoided. This is particularly true with particle laden gas streams, such as for instance the exhaust gas of a diesel engine. Compared to the prior art, only volume streams that are significantly stronger have been controlled. In prior art methods, the entire dilutant stream must be controlled. In the present arrangement, only the controlled stream for the back-up region must be controlled. The so-called pneumatic diaphragm arrangement provides significant simplification in the apparatus required.

Since the pressure in the diluting system no longer has to be boosted at the admission side, additional heating of the dilutant stream which occurred with prior arrangement is avoided. This provides a simplification in comparison to the prior art and eliminates the necessity of cooling mechanisms which had to be necessary for apparatuses which increase the temperature of dilutant streams.

The present arrangement results in a considerably reduced structural size of an apparatus compared to apparatus which was intended to accomplish the same ends, and this is a significant advantage. In comparison with prior structures which employed a relatively large pressure blower at the input side of the actual diluting system, these can be omitted. This means that an exhaust arrangement which is significantly reduced in size or volume can be utilized at the output side. Where an apparatus is to be used in an engine testing bench, for example, a significant advantage is established over prior art devices that were roughly twice as large in design.

In accordance with a further feature of the method of the invention, a control stream is directly branched out of the dilutant stream before mixing with the sub-quantity and the control stream is compressed before being supplied to the back-up region. A control line is provided between the delivery line of the dilutant stream and the removal line of the sub-quantity and a blower is employed in the control line. Although the control stream can be fundamentally supplied entirely independently of the dilutant stream, for example, from a different source or different carrier, marking gases such as nitrogen or the like, which can also be used for various applications, a significant advantage derives from the present design in that the control stream can be branched from the supplied dilutant stream after the potential cooling, filtering and volume stream measurement and the like. This enables a further reduction in apparatus related outlay.

In a further feature of the invention, the pressure and/or volume of the control stream is controlled dependent on the pressure of the averaged pressure of the dilutant gas stream. Reactions to the fluctuations of the dilutant gas stream can thus be immediately carried in a simple manner and the volume stream of the sub-quantity for mixing with the dilutant stream will remain representative of the main gas stream from which the test amount is taken.

In a further feature of the invention, cooling of the dilutant stream takes place before the filtering. The dilutant stream is cooled and filtered because a temperature of the dilutant stream that is excessively high from the outset is avoided, and this also avoids the introduction of impurities via the dilutant stream. This yields the advantage that the cooler utilized for this purpose need not be constructed of expensive equipment. In the utilization of prior art initially discussed, a cooling of the dilutant stream must be provided following the compression at the input end and this occurs after the filtering that precedes the compressor. In that arrangement, it must be provided that impurities are not reintroduced into the dilutant stream due to soot particles peeling off the cooler. For this reason, the cooler must be comprised of stainless steel, and this has an additional disadvantage in that larger cooling surfaces are required because of lower thermal conductivity of stainless steel.

In a further feature of the apparatus of the present invention, the back-up region is located in the downstream side of the sub-quantity removal stream. This affords improved accessibility. It also makes it possible for immediate influencing of the volume stream of the sub-quantity in the region of its emergence from the sub-quantity line for mixing with the dilutant stream.

In a further feature of the invention, in one preferred embodiment, the discharge of the control line in the back-up region of the removal line for the sub-quantity includes one or more control openings in the inside circumference of the removal line. This provides a structure where a deposit of particles or the like from the branched off sub-quantity is avoided. In another preferred embodiment of the invention, the region of the control line adjoining the control openings is directed opposite the flow direction of the sub-quantity. A desired "diaphragm" effect is thereby improved in a simple and effective way by the control stream emerging from the control line in counter-current direction to the sub-quantity flow and the diaphragm effect can be influenced by a specific alignment of the discharge region. In another preferred embodiment of the invention, the discharge of the control line in the back-up region of the sub-quantity removal line is formed by a discharge pipe section centrally directed against the flow in the removal line. In this simple embodiment, nothing need be modified at the removal line itself. The diaphragm effect is achieved by counter-current insufflation of the control stream.

In a further feature of the invention for controlling the control stream which is supplied to the back-up region, a blower in the control line can be controlled with respect to pressure and/or volume of the control stream. This affords a structurally simple solution without the necessity of employing additional component parts.

In a further preferred embodiment of the invention, a controllable throttle element can be arranged in the control line between the blower and back-up region. This provides a structure which influences the volume stream and pressure of the control stream, and in one form is provided with a control opening or openings which are adjustable in cross-section. A single control opening can be provided in the form of an annular gap, for example, and can have its cross-section adjusted in a simple way where two parts of the removal line limit the annular gap by being movable relative to one another.

In a further embodiment for influencing the control stream, a by-pass is employed having an adjustable pressure reduction valve in the control line following the blower. This yields a constant pressure of the control stream with a varying volume stream.

Other objects, advantages and features of the invention will become more apparent with the teaching of the principles thereof in connection with the disclosure of the preferred embodiments in the specification, claims and drawings, in which:

DESCRIPTION OF THE PREFERRED EMBODIMENTS

Figure 1:
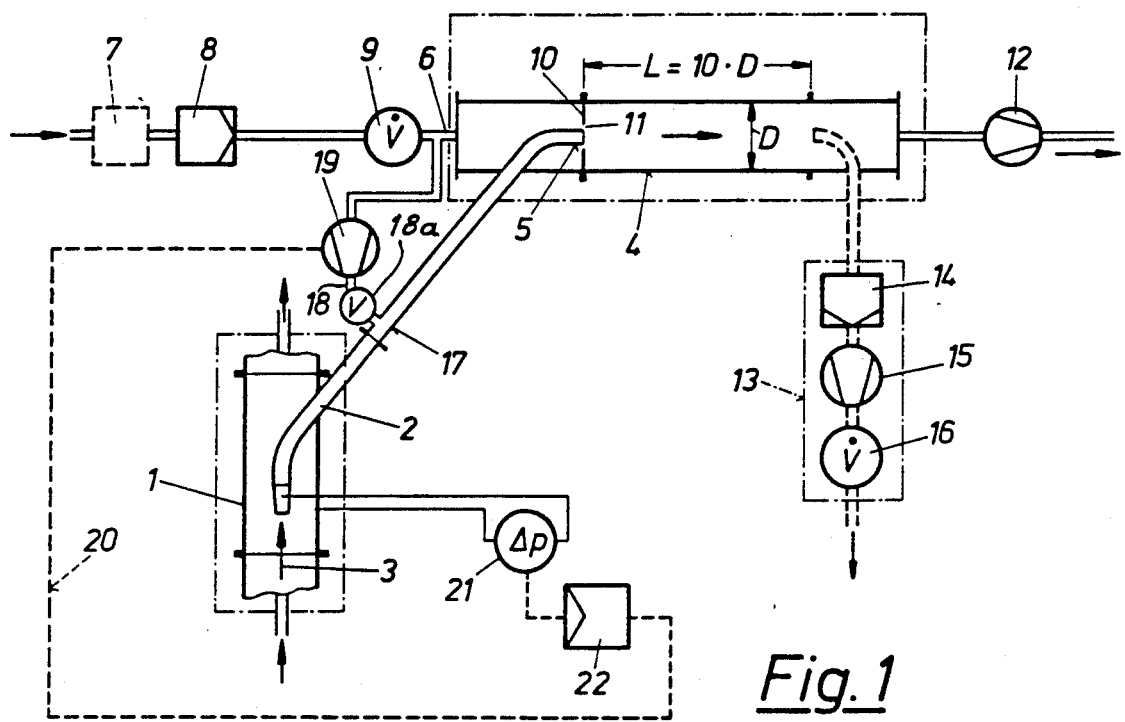
FIG. 1 is an overall schematic illustration of an apparatus constructed and operating with the principles of the present invention.

As illustrated in FIG 1, an apparatus is schematically shown for continuous removal of a sub-quantity from a gas stream and for the continuous mixing of this sub-quantity with a gaseous dilutant stream. While the arrangement may be employed in various commercial or laboratory arrangements for the continuous measurement of a flowing gas stream, for purposes of the description herein, the apparatus will be described in connection with the measurement of the exhaust gas of a diesel engine.

In FIG. 1 a main gas flow line 1 is shown which may carry the exhaust from a diesel engine. A sub-quantity removal line 2 is illustrated which branches the sub-quantity out of the exhaust gas stream 1. A sub-quantity is supplied to a mixing tunnel 4.

The sub-quantity removal line 2 projects with an open end facing upstream in the main gas flow stream flowing in the direction indicated by the arrowed line 3.

A downstream end 5 of the sub-quantity removal line 2 discharges into the mixing tunnel. The mixing tunnel also receives a dilutant gas stream which is delivered to the mixing tunnel through a delivery line 6 with the dilutant stream and sub-quantity stream thoroughly intermixing in the downstream end of the mixing tunnel. The dilutant stream carries a gas, such as ambient air, which is first passed through a cooler 7 which is used only as needed. Thereafter, the ambient air dilutant stream flows through a filter unit 8 and through a measuring unit 9 for measuring the stream volume. The dilutant stream flows into the upstream end of the mixing tunnel 4 and an annular gap 11 is provided by a fixed diaphragm 10 extending across the mixing tunnel. The downstream end 5 of the removal line exhausts into the gap for thorough mixing of the substream gas and the dilutant gas. The continued flow of mixed gases passes out of the mixing tunnel through a controllable exhauster 12 which is at the output end of the tunnel 4.

A sub-quantity of test gas supplied by the removal line 2 is uniformly mixed with the dilutant stream entering at the annular gap 11 and is thoroughly mixed under turbulent flow conditions to simulate emission conditions. The downstream end of the mixing tunnel, which defines the mixing path, has a preferred dimension, with a length L which is ten times the diameter D of the tunnel. This is indicated by the dimension line shown in FIG. 1.

The mixed substream and dilutant stream provide a diluted gas where a small portion is bled off by a measuring instrument 13. The gas is bled off through a simple small pipe preferably formed of electrically conductive material. The measuring instrument 13 operates as a particle collecting means and includes a filter unit 14, a pump 15, and a gauge 16 for measuring volume flow. This serves the purpose of depositing the particles which were originally contained in the main gas flow stream onto a filter unit for further evaluation. The filter unit 14 is usually constructed of a Teflon coated fiberglass.

Since the mean value of the main gas stream flow in the flow line 1 can fluctuate not only according to the motor cycle, but also due to various influences such as motor setting and operation, these will be in contrast to the pressure prevailing in the mixing tunnel 4. Pressure prevailing in the removal line 2 is defined by the essentially constant internal pressure of the mixing tunnel 4. Therefore, control of the volume of the stream of the sub-quantity flowing through the line 2 becomes necessary. For this purpose, a back-up region 17 is provided in the removal line 2. In this back-up region 17 is a control line 18 that carries a control stream from a blower 19 which is controllable dependent upon the pressure of the gas stream in the line upstream of the blower.

As illustrated, a control line 18 is provided supplied from the delivery line 6 of the dilutant stream. The control line leads into the removal line 2 of the sub-quantity. In a modification thereof, the control stream for control line 18 could be supplied through the back-up region 17 independently of the dilutant stream. In this case, instead of the control of the blower 19 being dependent upon the dilutant stream line 6, line 20 could be arranged to lead into the blower connected to a pressure difference transmitter 21 which measures the difference in pressure between the removal line 2 and the main line 1. This would control the value at 22. Thus, the transmitter 21, controlling the value at 22 thereby controlling the blower 19 regulates the pressure of the control stream as a function of the pressure, preferably the averaged pressure of the main gas stream. Air supplied to the blower would still be obtained from the dilutant line 6. In this arrangement, a control valve 18a could also be provided in the control line 18 downstream of the blower to insure a constant pressure in the control stream independently of the volume.

In the arrangement, a control stream is introduced into the back-up region 17 in a controlled manner, providing a "pneumatic diaphragm" effect. This enables a control of the volume stream of the sub-quantity emerging at the downstream end 5 of the sub-quantity removal line 2 without any mechanical constriction and without influencing of the cross-section of the removal line 2.

Figure 2:
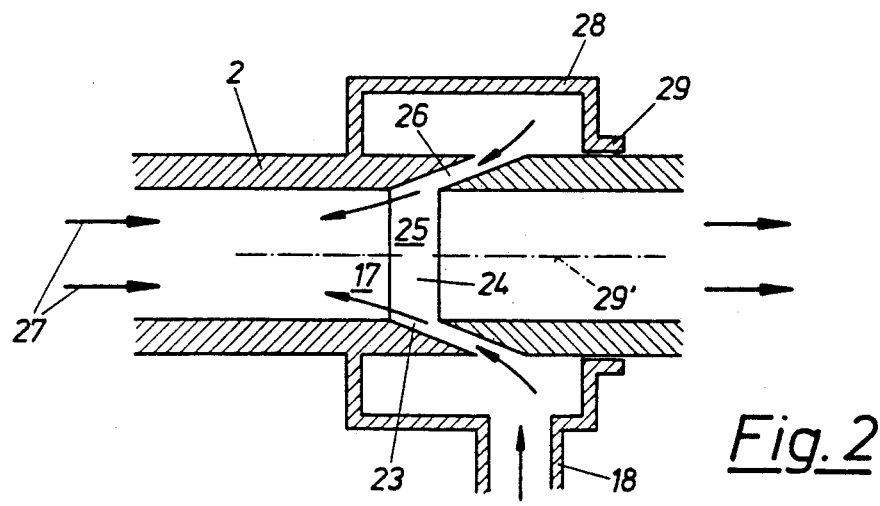
FIG. 2 is an enlarged schematic showing of a portion of the back-up region of the sub-quantity line of the apparatus.

According to the details shown in FIG. 2, which illustrates the general area of the back-up region 17, the structure includes a control opening 25 which is formed as an annular gap 24 surrounding the sub-quantity line 2. A discharge of gas into the sub-quantity removal line 2 is directed essentially opposite the flow direction of the sub-quantity, which flow direction is indicated by the arrowed lines 27. A counter-current effect is thus created as a result of the control stream entering under over-pressure relative to the pressure of the flow through the line 2, and this promotes the action of the pneumatic diaphragm.

FIG. 2 illustrates a delivery of a control stream which is uniform over the circumference of the removal line 2. A housing 28 surrounds the annular gap 26. This housing is constructed so that it can be moved back and forth in the direction of the axis shown at 29'. If the housing 28 is moved back and forth in the direction of the axis 29', the effective size of the annular gap 24 or, in other words of the control opening 25, is varied. This enables a control of the control stream similar to the aforementioned arrangement of a throttle element between the blower and back-up region.

Figure 3:
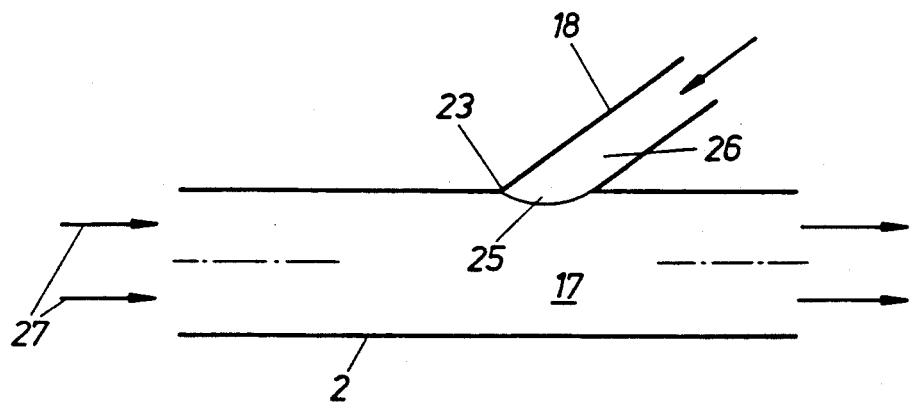
FIGS. 3 through 5 are enlarged schematic detailed views similar to FIG. 2 but illustrating other arrangements for the structure of back-up regions in the sub-quantity removal line of the apparatus.

In the embodiment shown in FIG. 3, a single control opening is provided at 25 in the circumference of the removal line. This opening accommodates the discharge 23 of the control line 18 in the back-up region of the removal line 2. A control flow 26 through the interior of the control line 18 is directed opposite the flow direction of the sub-quantity, which flow is indicated by the arrows 27.

Figure 5:
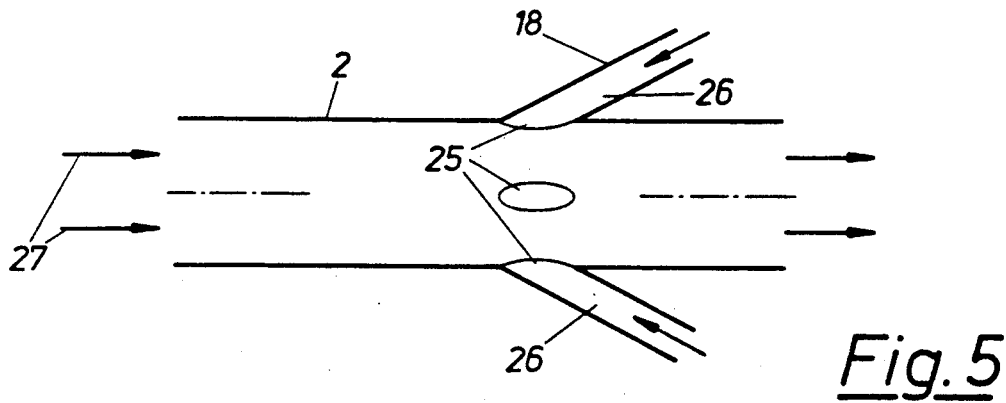

FIG. 5 illustrates another embodiment similar to FIG. 3, but a plurality of control openings are shown at 25 arranged around the circumference of the removal line 2. Again, the flow from the control line proceeds opposite the flow of the sub-quantity through the line 2.

Figure 4:
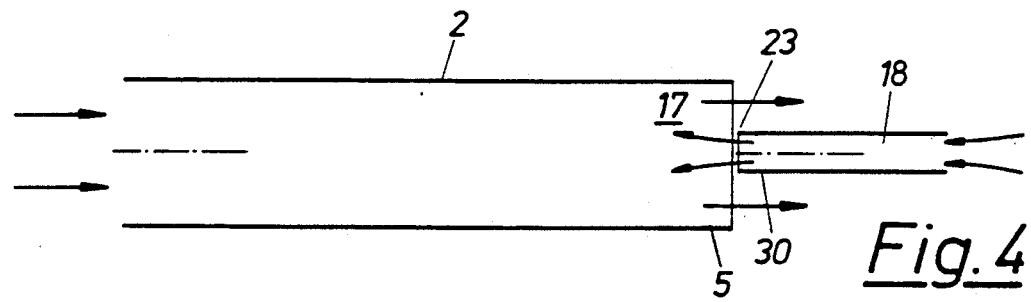

In the embodiment of FIG. 4, a discharge 23 from the control line 18 is directed into the removal line by a small discharge pipe section 30 which is coaxially and centrally located within the removal line 2. This is located at the downstream end 5 of the removal line, and the discharge pipe section 30 insufflates the control stream directly into the downstream end of the removal line 2.

In operation, the substream line 2 provides for the continual removal of a substream from the main flow line 1 which may be a line such as the exhaust of a diesel engine. The substream flows up into the mixing tunnel 4 where it mixes with a dilutant stream which flows through an annular gap 11 at the upstream end of the mixing tunnel. The volume stream of the sub-quantity is controlled by a control line 18 in a back-up region in the sub-quantity line 2. The flow through the control line 18 is provided by a blower 19 receiving a supply from the dilutant line 6. The control flow through the control line is directed in a direction counter to the flow through the sub-quantity line 2 without the dimension of the sub-quantity line 2 being affected. The counter-control line flow may be provided by an annular gap 24, FIG. 2, by a single opening 25, FIG. 3, by multiple circumferentially spaced openings, FIG. 5, or by a small line, FIG. 4. In each instance, the controlling flow from the control line 18 into the back-up region is directed in counterflow, or contrary to the direction of flow of the sub-quantity of gas. Thus, the relationship between the dilution gas and the sub-quantity flow is accurately and simply controlled by control of the flow of the sub-quantity which removes a representative sub-quantity from the main flow line. The composition of the sub-quantity is not affected. The dilutant stream is not affected and the necessity of providing for compressor losses and cooling of the dilution gas which was necessary seen that there has been provided an improved method and apparatus for the removal of a sub-quantity from a gas stream and the continuous mixing with a gaseous dilutant stream.

We claim as our invention:

1. A method for the continuous removal of a sub-quantity of gas from a main gas stream for continuous mixing of the sub-quantity with a dilutant gas stream, comprising the steps:
   receiving a sub-quantity of gas flow from a main gas stream;
   directing the sub-quantity to mix with a volume of dilutant gas;
   passing the sub-quantity through a back-up region before mixing with the dilutant gas;
   and supplying a controllable control stream of gas to said back-up region at a pressure greater than the pressure of the sub-quantity and controlling the flow volume of the sub-quantity by controlling the control stream.

2. A method for the continuous removal of a sub-quantity of gas from a main gas stream and mixing with a gaseous dilutant stream in accordance with the steps of claim 1:
   including obtaining the control stream from the dilutant stream before the dilutant stream is mixed with the sub-quantity and compressing the control stream for delivery to the back-up region.

3. A method for the continuous removal of a sub-quantity of gas from a main gas stream and mixing with a gaseous dilutant stream in accordance with the steps of claim 1:
   including regulating the pressure of the control stream as a function of the averaged pressure of the main gas stream.

4. A method for the continuous removal of a sub-quantity of gas from a main gas stream and mixing with a gaseous dilutant stream in accordance with the steps of claim 1:
   including filtering and cooling the dilutant gas stream and cooling the dilutant stream before it is filtered.

5. A method for the continuous removal of a sub-quantity of gas from a main gas stream and mixing with a gaseous dilutant stream in accordance with the steps of claim 1 :
   including the step of controlling the stream of gas to the back-up region as a function of the pressure of the gas stream flowing in the main gas stream.

6. An apparatus for the continuous removal of a sub-quantity of gas from a main gas stream and mixing the sub-quantity with a gas dilutant stream, comprising in combination:
   a main gas flow line;
   a sub-quantity line branching from the flow line for removal of a sub-quantity of gas;
   means for supplying a dilutant gas;
   a mixing chamber connected to receive dilutant gas and sub-quantity gas for mixing said gases therein;
   a back-up region through which the sub-quantity line extends before discharging into said mixing chamber;
   a control line carrying a control stream of gas connected to the back-up region for controlling the flow of sub-quantity gas into the mixing chamber;
   and means controlling delivery of the control line as a function of pressure in the main line.

7. An apparatus for the continuous removal of a sub-quantity of gas from a main gas stream and mixing the sub-quantity with a gas dilutant stream constructed in accordance with claim 6:
   wherein said control line is connected to said supply means for dilutant gas receiving dilutant gas prior to its entering the mixing chamber;
   and a blower in said control line.

8. An apparatus for the continuous removal of a sub-quantity of gas from a main gas stream and mixing the sub-quantity with a gas dilutant stream constructed in accordance with claim 6:
   wherein said sub-quantity line has a discharge end leading into said mixing chamber;
   and said back-up region is located at the discharge end of the sub-quantity line.

9. An apparatus for the continuous removal of a sub-quantity of gas from a main gas stream and mixing the sub-quantity with a gas dilutant stream constructed in accordance with claim 6:

wherein the control line opens in at least one control opening at the inside circumference of the sub-quantity line.

10. An apparatus for the continuous removal of a sub-quantity of gas from a main gas stream and mixing the sub-quantity with a gas dilutant stream constructed in accordance with claim 9:
   wherein said opening is directed opposite the flow direction of the sub-quantity of gas in the sub-quantity line.

11. An apparatus for the continuous removal of a sub-quantity of gas from a main gas stream and mixing the sub-quantity with a gas dilutant stream constructed in accordance with claim 6:
   wherein the sub-quantity line has a downstream end discharging into the mixing chamber and the control line has a discharge end directed coaxially against the downstream end of the sub-quantity line.

12. An apparatus for the continuous removal of a sub-quantity of gas from a main gas stream and mixing the sub-quantity with a gas dilutant stream constructed in accordance with claim 6: including a blower in the control line with means for controlling the blower as a function of the flow of gas in the main flow line.

13. An apparatus for the continuous removal of a sub-quantity of gas from a main gas stream and mixing the sub-quantity with a gas dilutant stream constructed in accordance with claim 6:
   including a blower in the control line and a control valve positioned between the blower and said back-up region.

14. An apparatus for the continuous removal of a sub-quantity of gas from a main gas stream and mixing the sub-quantity with a gas dilutant stream constructed in accordance with claim 6:
   wherein the control line terminates in at least one opening in said back-up region with means for adjusting the cross-sectional area of said control opening.

15. An apparatus for the continuous removal of a sub-quantity of gas from a main gas stream and mixing the sub-quantity with a gas dilutant stream constructed in accordance with claim 6:
   including a blower in the control line and a control valve downstream of the blower and means for controlling the blower and valve to obtain constant pressure in the control line.

16. A method for the continuous removal of a sub-quantity of gas from a main gas stream and mixing the sub-quantity with a dilutant gas stream, comprising the steps:
   supplying a volume of dilutant gas to a mixing chamber;
   removing a flow of sub-quantity gas from a main stream delivering it to the mixing chamber;
   controlling the flow of the sub-quantity of gas by a stream of control gas;
   and directing the stream of controlled gas in a counterflow direction to the flow direction of the sub-quantity for varying the flow volume of the sub-quantity flowing to the mixing chamber.

17. A method for the continuous removal of a sub-quantity of gas from a main gas stream and mixing the sub-quantity with a dilutant gas stream in accordance with steps of claim 16:
   wherein the controlled gas is obtained from the supply of dilutant gas prior to its being mixed with the sub-quantity.

18. A method for the continuous removal of a sub-quantity of gas from a main gas stream and mixing the sub-quantity with a dilutant gas stream in accordance with steps of claim 16:
   including varying the pressure of the controlled gas as a function of the pressure of gas in said main stream.

19. In a diesel engine, the combination comprising:
   an exhaust line for carrying off the exhaust of a diesel engine;
   a sub-quantity line branching from the exhaust line for the removal of a sub-quantity of exhaust gas;
   means for supplying a dilutant gas;
   a mixing chamber connected to receive dilutant gas and sub-quantity gas;
   a back-up region through which the sub-quantity line extends before discharging into said mixing chamber;
   a control line carrying a control stream of gas connected to the back-up region and controlling the flow of sub-quantity of gas to the mixing chamber;
   and means controlling delivery of the control gas for controlling the volume of sub-quantity gas delivered to the mixing chamber.

* * * * *